(12) United States Patent
Iida (10) Patent No.: US 8,481,973 B2
(45) Date of Patent: Jul. 9, 2013

(54) FLUORESCENT ESTIMATING APPARATUS, FLUORESCENT ESTIMATING METHOD, AND FLUORESCENT MEASURING APPARATUS

(75) Inventor: Yoshiko Iida, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 50 days.

(21) Appl. No.: 13/196,191

(22) Filed: Aug. 2, 2011

(65) Prior Publication Data

US 2012/0043478 A1    Feb. 23, 2012

(30) Foreign Application Priority Data

Aug. 18, 2010    (JP) ................................. 2010-183392

(51) Int. Cl.
*G01N 21/64* (2006.01)
(52) U.S. Cl.
USPC ..................................... 250/459.1; 250/458.1
(58) Field of Classification Search
USPC ........................................................ 250/459.1
See application file for complete search history.

(56) References Cited

U.S. PATENT DOCUMENTS

| 6,535,278 | B1* | 3/2003 | Imura ............................. 356/73 |
| 2002/0135768 | A1* | 9/2002 | Sugiyama et al. ............ 356/405 |
| 2006/0092444 | A1* | 5/2006 | Nakamura et al. ............. 358/1.9 |
| 2006/0192957 | A1* | 8/2006 | Frick et al. ..................... 356/328 |
| 2006/0227319 | A1* | 10/2006 | Imura ............................. 356/256 |
| 2007/0086009 | A1* | 4/2007 | Ehbets et al. .................. 356/402 |
| 2008/0308740 | A1* | 12/2008 | Wegmuller et al. ........... 250/372 |

FOREIGN PATENT DOCUMENTS

JP    2006-84333    3/2006

OTHER PUBLICATIONS

Koshin Mihasi, Fluorescent Measurement, Chapter II, The Spectroscopical Society of Japan, Measuring Method Series, Japan Scientific Societies Press, pp. 45-55 (1983).

* cited by examiner

*Primary Examiner* — Marcus Taningco
(74) *Attorney, Agent, or Firm* — Fitzpatrick, Cella, Harper & Scinto (57) ABSTRACT

This invention provides a technique for efficiently estimating spectral radiance factors of fluorescence of a sample. To this end, for a sample which contains a fluorescent substance, first spectral reflectance data and second spectral reflectance data are obtained by making two different variable-angle measurements using a general colorimeter under a white light source. Ratios n of the first spectral reflectance data to the second spectral reflectance data in a long-wavelength spectrum range outside a fluorescent spectrum range of the sample are calculated. Then, difference data between spectral reflectance data as results of multiplying the second spectral reflectance data by the ratios n, and the first spectral reflectance data are calculated. The difference data are divided by values obtained by subtracting 1 from the ratios n, thereby calculating spectral reflectances of fluorescence of the sample, that is, spectral radiance factors.

16 Claims, 7 Drawing Sheets

| SPECTRAL REFLECTANCE DA | | | | | 1501 |
|---|---|---|---|---|---|
| WAVELENGTH λ | 380 | 390 | ..... | 780 | |
| REFLECTANCE | | | | | |

| SPECTRAL REFLECTANCE DB | | | | | 1502 |
|---|---|---|---|---|---|
| WAVELENGTH λ | 380 | 390 | ..... | 780 | |
| REFLECTANCE | | | | | |

FIG. 16

| FLUORESCENCE P | | | | | 1601 |
|---|---|---|---|---|---|
| WAVELENGTH λ | 380 | 390 | ....... | 780 | |
| RADIANCE FACTOR | | | | | |

FLUORESCENT ESTIMATING APPARATUS, FLUORESCENT ESTIMATING METHOD, AND FLUORESCENT MEASURING APPARATUS

BACKGROUND OF THE INVENTION

1. Field of the Invention

The present invention relates to a technique for acquiring spectral radiance factors of fluorescence.

2. Description of the Related Art

A material that produces fluorescence (for example, a fluorescent substance such as a fluorescent whitener) is often used in a print medium and color materials used in an image output operation, so as to enhance the whiteness of the print medium and to revive colors of the color materials. The fluorescent substance has a property of emitting light within a visible light range when it is exposed with light outside the visible light range represented by ultraviolet rays. As a result, the color reproducibility of a printed matter varies depending on differences of illumination light used to view an output image. Therefore, in an image processing apparatus which uses a print medium and color materials containing a fluorescent substance, in order to faithfully estimate reproduced colors of an output image under an arbitrary viewing environment, it is required to acquire spectral radiance factors due to light emission of the fluorescent substance contained in the print medium and color materials.

In general, spectral reflectances of a sample are measured by exposing the sample with light coming from a white light source, receiving reflected light by a spectroradiometer to measure spectral reflection intensities, and dividing the spectral reflection intensities by a spectral intensity of the white light source. However, with this measurement method, the spectral reflection intensities of the sample cannot be separated into reflection elements due to regularly reflected light and diffuse light, and fluorescent elements due to emission (fluorescence) of the fluorescent substance. Therefore, fluorescent-dependent spectral reflectances of the measured spectral reflectances, that is, spectral radiance factors of fluorescence alone cannot be acquired.

Therefore, in order to measure fluorescence emitted by a sample, the following technique has been proposed. A method of measuring spectral reflectances of a sample under two different light sources, and estimating a fluorescent amount under a viewing light source based on a ratio between a light energy sum total in an excitation spectrum range and a light energy sum total in an emission spectrum range of the respective light sources is known (for example, Japanese Patent Laid-Open No. 2006-84333; to be referred to as literature 1 hereinafter). Also, a technique which configures a colorimeter that measures fluorescence alone is known (for example, Koshin Mihasi, "Fluorescent measurement", The Spectroscopical Society of Japan, Measuring Method Series, Japan Scientific Societies Press, 1983; to be referred to as literature 2 hereinafter). According to this technique, arbitrary short-wavelength light in a spectrum range outside the visible light range is extracted from light coming from a measuring light source via a spectroscope as incident light. Then, fluorescence yielded by exposing a sample with the incident light is input to a detector via the spectroscope again.

However, the conventional fluorescent measuring method suffers the following problems.

With the technique described in literature 1, since the fluorescent amount of the sample under the viewing environment is calculated from measurement values under the two light sources, the two different light sources have to be prepared, thus complicating the arrangement of a colorimeter.

A fluorescent measuring apparatus described in literature 2 requires a spectroscope to generate incident light onto the sample, thus also complicating the arrangement of the colorimeter. Furthermore, since a spectral radiant energy of short-wavelength light acquired from the light of the measuring light source via the spectroscope lowers, a spectral reflectance energy of fluorescence emitted by the sample with respect to the incident light also lowers. For this reason, it is difficult to detect fluorescence by the detector, resulting in poor measurement precision. Hence, the detection precision of the detector has to be improved to be higher than a general spectroradiometer, or an amplifier which enhances the lowered spectral reflectance energy of fluorescence is also required. Therefore, the arrangement of the fluorescent measuring apparatus based on the above technique is further complicated as a specific apparatus compared to a general colorimeter. Also, in order to acquire fluorescence from the sample, light outside the visible light range has to be exposed. With the technique described in patent literature 1, in order to extract the incident light as short-wavelength light, a plurality of different short-wavelength light rays have to be incident in a range outside the visible light range, and have to be measured a plurality of times, thus requiring a larger number of measurement processes.

SUMMARY OF THE INVENTION

The present invention has been made to solve the aforementioned problems, and provides a technique for efficiently estimating spectral radiance factors of fluorescence of a sample.

In order to solve the above-described problems, for example, the present invention in its aspect provides a fluorescent estimating apparatus comprising: an acquisition unit configured to acquire, for a sample which is likely to contain a fluorescent substance, first spectral reflectances measured at a first measuring angle and second spectral reflectances which are measured at a second measuring angle and are higher than the first spectral reflectances, under a measuring light source which emits light in a spectrum range including an excitation spectrum range and a fluorescent spectrum range of the fluorescent substance, and a long-wavelength spectrum range outside the fluorescent spectrum range; a ratio calculation unit configured to calculate ratios of the second spectral reflectances to the first spectral reflectances in the long-wavelength spectrum range; a difference calculation unit configured to calculate differences between products obtained by multiplying the first spectral reflectances by the ratios, and the second spectral reflectances; and a fluorescent calculation unit configured to calculate spectral radiance factors of fluorescence of the sample based on the differences and the ratios.

According to the present invention, the spectral radiance factors of fluorescence of a sample can be efficiently estimated.

Further features of the present invention will become apparent from the following description of exemplary embodiments (with reference to the attached drawings).

DESCRIPTION OF THE EMBODIMENTS

Embodiments of the present invention will be described hereinafter with reference to the drawings. Note that the following embodiments do not limit the present invention according to the scope of the claims, and all combinations of features described in the embodiments are not always essential for solving means of the present invention.

First Embodiment

System Arrangement

Figure 1:
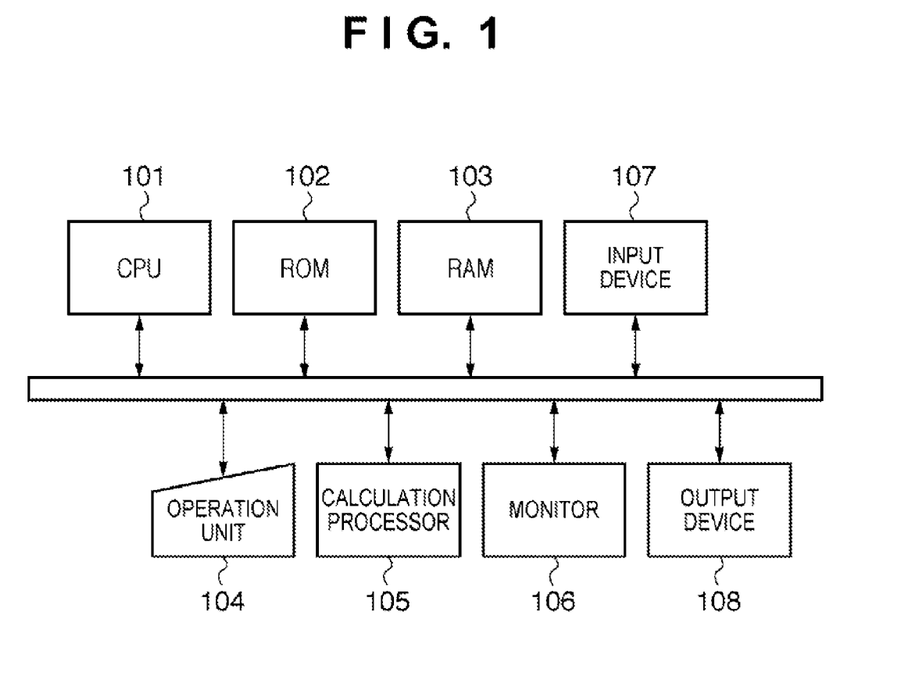
FIG. 1 is a block diagram showing the arrangement of an image processing apparatus according to the first embodiment.

FIG. 1 is a block diagram showing the arrangement of an image processing apparatus according to this embodiment. Referring to FIG. 1, a CPU 101 controls other components to be described below in accordance with, for example, control programs, OS, application programs, and device drivers stored in a ROM 102. Reference numeral 107 denotes an input device, which includes a measuring apparatus that acquire various kinds of measurement data according to the present invention. Reference numeral 108 denotes an output device, which includes, for example, a printer that outputs various kinds of measurement values and fluorescent data calculated by a calculation processor 105. A RAM 103 is used as a work area and temporary saving area of various kinds of control programs and data input from an operation unit 104.

The operation unit 104 is used to input, for example, measurement data acquired by the input device 107. The calculation processor 105 executes, for example, calculation processing required to estimate spectral radiance factors of fluorescence in this embodiment. Reference numeral 106 denotes a monitor which displays, for example, the processing result of the calculation processor 105 and data input by the operation unit 104 in the same manner as the output device 108.

Principle of Fluorescent Estimation

The principle of a method of estimating spectral radiance factors of fluorescence according to this embodiment will be described below.

Figure 8:
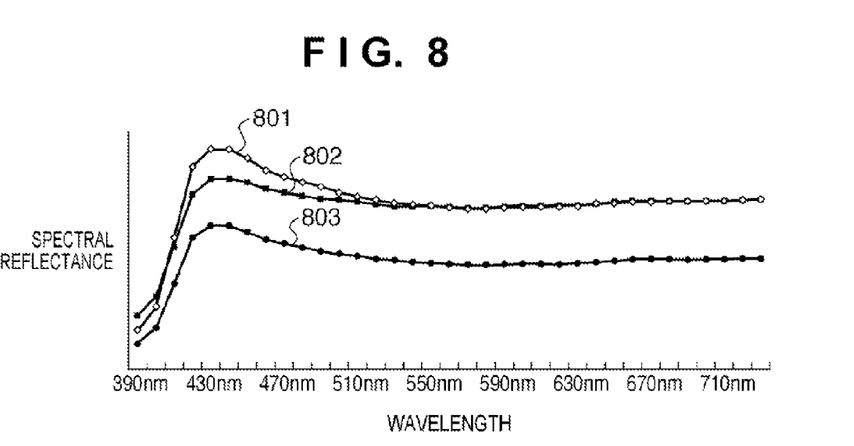
FIG. 8 is a graph showing an example of spectral reflectances of a print medium, which are acquired by variable-angle measurements, according to the first embodiment.

FIG. 8 is a graph showing spectral reflectances, which are acquired by making variable-angle measurements of a print medium containing a fluorescent substance under a measuring light source. Note that a white light source which emits light in the following broad spectrum range is used as the measuring light source in this case. For example, this white light source emits light in a spectrum range including an excitation spectrum range (for example, 300 to 400 nm) and fluorescent spectrum range (for example, 400 to 580 nm) of the fluorescent substance contained in the print medium, and a long-wavelength spectrum range (for example, 580 to 780 nm) outside the fluorescent spectrum range. In FIG. 8, a spectral reflectance curve 802 represents a measurement result acquired by arranging the light source and a spectroradiometer to make an angle (angle of incidence:angle of reflection=45°:45°), at which the spectroradiometer receives regular reflected light of the light source, with respect to the print medium as a sample. Also, a spectral reflectance curve 803 represents a measurement result acquired by arranging the light source and spectroradiometer to make an angle (for example, angle of incidence:angle of reflection=45°:0°), at which the spectroradiometer is allowed to measure only diffuse light that does not contain regular reflected light of the light source, with respect to the print medium. As can be seen from FIG. 8, spectral reflectances to be acquired change according to the angles the light source and spectroradiometer make with respect to the print medium, that is, measuring angles.

Figure 7:
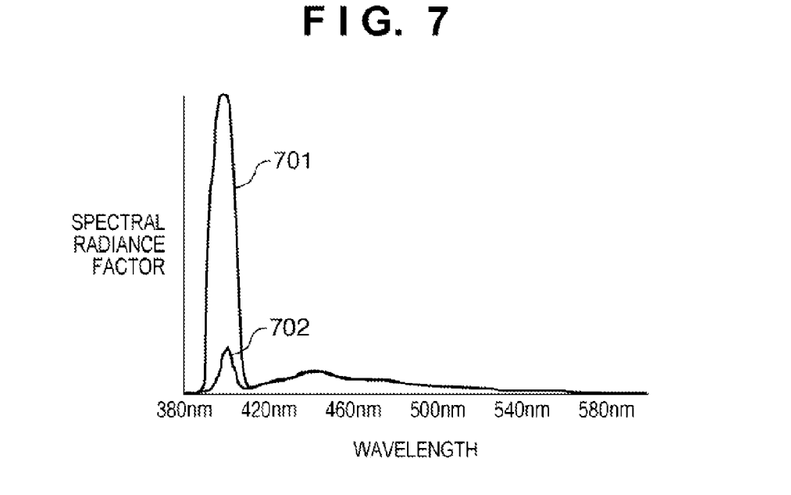
FIG. 7 is a graph showing the relationship between the measuring angles and spectral radiance factors of fluorescence according to the first embodiment.

FIG. 7 is a graph showing results acquired when fluorescence produced by exposing the print medium with short-wavelength light of 400 nm is measured at different angles. Referring to FIG. 7, a spectral radiance factor curve 701 represents a measurement result acquired when the light source and spectroradiometer are arranged at positions where the regular reflected light can be measured (angles of incidence and reflection=45°) to have a certain print medium as a sample. Also, a spectral radiance factor curve 702 represents a measurement result acquired when the light source and spectroradiometer are similarly arranged at positions where the diffuse light alone can be measured (angle of incidence=45°, angle of reflection=0°) with respect to the print medium. As can be seen from FIG. 7, the radiance factors for the short-wavelength light of 400 nm change depending on the measuring angles, but the radiance factors obtained in the fluorescent spectrum range of 420 to 580 nm in which fluorescence is produced (that is, the radiance factors of fluorescence) are nearly constant irrespective of the measuring angles. The same tendencies are observed not only for the radiance factors on the print medium but also for those on a color material applied on the print medium.

As can be seen from the above description, in reflected light from the print medium or color material, the spectral reflectances of reflection elements caused by the regular reflected light and diffuse light have properties in which their values change depending on the measuring angles (to be referred to as angle relativity hereinafter). On the other hand, as can be seen from the above description, the spectral radiance factors of fluorescent elements depending on the fluorescent substance have no angle relativity. In this embodiment, the spectral reflectances (that is, spectral radiance factors) of fluorescent elements (that is, fluorescence) are estimated from variable-angle measurement results with respect to a sample using angle relativity differences of the reflection and fluorescent elements in reflected light from the sample.

In the following description, note that a term "fluorescent element" in reflected light from a sample is used synonymously with "fluorescence" produced by a fluorescent substance contained in the sample. Therefore, the "spectral reflectances of fluorescent elements" in the reflected light are synonymous with the "radiance factors of fluorescence".

A method of acquiring the spectral reflectances of fluorescence (that is, the spectral radiance factors of fluorescence) based on the angle relativity differences will be described below. Note that the following description will be given using the graph shown in FIG. 14 which extracts features of the measurement values of the spectral reflectances shown in FIG. 8, so as to allow to visually recognize the angle relativity differences. A spectral reflectance curve 1402 shown in FIG. 14 corresponds to the spectral reflectance curve 802 shown in FIG. 8, and represents a measurement result acquired at the angle where the regular reflected light can be measured. Likewise, a spectral reflectance curve 1403 corresponds to the spectral reflectance curve 803, and represents a measurement result acquired at the angle where the diffuse light alone can be measured.

Figure 14:
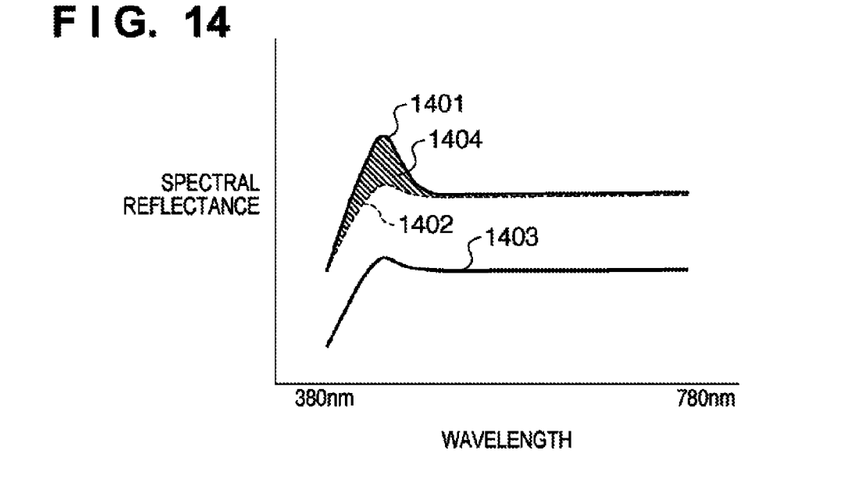
FIG. 14 is a graph which extracts features of the graph shown in FIG. 8.

Each of the spectral reflectance curves 1402 and 1403 is acquired to be defined by values obtained by combining spectral reflectances $R(\lambda)$ of reflection elements caused by the regular reflected light and diffuse light, and spectral reflectances $P(\lambda)$ of fluorescent elements, since the reflected light at the time of measurement contains fluorescence. As described above, the spectral reflectances $R(\lambda)$ of the reflection elements vary due to the angle relativity, but the spectral reflectances $P(\lambda)$ of the fluorescent elements can be commonly used since they have no angle relativity. Therefore, the spectral reflectance curves 1402 and 1403 can be respectively expressed by $R1(\lambda)+P(\lambda)$ and $R2(\lambda)+P(\lambda)$ using only different spectral reflectances of the reflection elements.

In FIG. 14, values (ratios) n to be multiplied by the lower spectral reflectance curve 1403 are decided, so that the spectral reflectance curves 1402 and 1403 are equivalent to each other in a long-wavelength spectrum range (580 to 780 nm) outside a visible range (380 to 580 nm) including the spectral reflectances of the fluorescent elements. Then, results obtained by multiplying the spectral reflectance curve 1403 by the ratios n are obtained as a spectral reflectance curve 1401. As shown in FIG. 14, the spectral reflectance curve 1401 obtained by multiplying the spectral reflectance curve 1403 by n does not match the spectral reflectance curve 1402.

As described above, the spectral reflectance curve 1403 is expressed by a sum of the spectral reflectances $R2(\lambda)$ of the reflection elements and the spectral reflectances $P(\lambda)$ of the fluorescent elements, that is, $R2(\lambda)+P(\lambda)$. Then, the spectral reflectance curve 1401 can be expressed as a curve obtained by simply multiplying the spectral reflectance curve 1403 by n. Also, since the spectral reflectance curve 1402 corresponds to n multiples of the spectral reflectance curve 1403 in the long-wavelength spectrum range including no fluorescent elements, the spectral reflectances $R1(\lambda)$ of the reflection elements in the spectral reflectance curve 1402 correspond to n multiples of the spectral reflectances $R2(\lambda)$ of the reflection elements in the spectral reflectance curve 1403. Therefore, the spectral reflectance curve 1402 is expressed by a curve defined by further adding the common spectral reflectances $P(\lambda)$ of the fluorescent elements to n multiples of the spectral reflectances $R2(\lambda)$ of the reflection elements. The spectral reflectance curves 1401, 1402, and 1403 are respectively expressed by:

Spectral reflectance curve 1401: $n \cdot (R2(\lambda)+P(\lambda))$
Spectral reflectance curve 1402: $n \cdot R2(\lambda)+P(\lambda)$
Spectral reflectance curve 1403: $R2(\lambda)+P(\lambda)$ Then, differences $D(\lambda)$ between the spectral reflectance curves 1401 and 1402 are calculated by:

$$D(\lambda) = n \cdot (R2(\lambda) + P(\lambda)) - (n \cdot R2(\lambda) + P(\lambda)) \qquad (1)$$
$$= (n-1) \cdot P(\lambda)$$

The differences $D(\lambda)$ correspond to a hatched part 1404 in FIG. 14.

Equation (1) can be modified to:

$$P(\lambda) = D(\lambda)/(n-1) \qquad (2)$$

As shown in equation (2), the spectral reflectance $P(\lambda)$ of each fluorescent element in a sample is calculated from the difference $D(\lambda)$ between the two spectral reflectances obtained by the variable-angle measurements, and the ratios n based on the measurement values. Note that for the purpose of range adjustment of fluorescent elements, equation (2) may be multiplied by an arbitrary coefficient $\alpha$, as given by:

$$P(\lambda) = (D(\lambda)/(n-1)) \cdot \alpha \qquad (3)$$

The spectral reflectances $P(\lambda)$ of the fluorescent elements, which are calculated, as described above, are the spectral radiance factors of fluorescence.

The above description has been given based on the graph of FIG. 14 which extracts features of the measurement results shown in FIG. 8. Of course, the spectral reflectances of the fluorescent elements can be calculated by the same processing even in FIG. 8. That is, ratios n are calculated so that the spectral reflectance curves 803 and 802 become equivalent to each other in the long-wavelength spectrum range containing no fluorescent elements, and a spectral reflectance curve 801 obtained by multiplying the spectral reflectance curve 803 by n is generated. Then, differences $D(\lambda)$ between the spectral reflectance curves 801 and 802 are calculated, thereby obtaining the spectral reflectances $P(\lambda)$ of the fluorescent elements using equation (2) or (3) as in FIG. 14.

Figure 9:
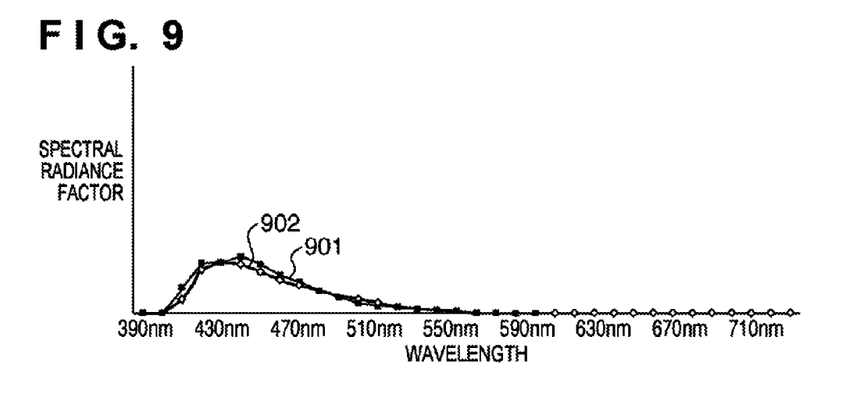
FIG. 9 is a graph showing an example of the spectral radiance factors of fluorescence of the print medium, which are estimated according to the first embodiment.

FIG. 9 shows a spectral radiance factor curve 901 of fluorescent elements, which is calculated using equation (2) above from two different types of variable-angle measurement data (spectral reflectances) for the print medium containing the fluorescent substance as the measurement target in FIG. 8. Note that FIG. 9 also shows a spectral radiance factor curve 902 of the fluorescent elements, which is measured using the conventional method. As can be seen from FIG. 9, the spectral radiance factor curve 901 of the fluorescent elements acquired by this embodiment nearly matches the spectral radiance factor curve 902 of the fluorescent elements measured by the conventional method and, therefore, the wavelength characteristics of the fluorescent elements can be acquired by the method of this embodiment.

Figure 10:
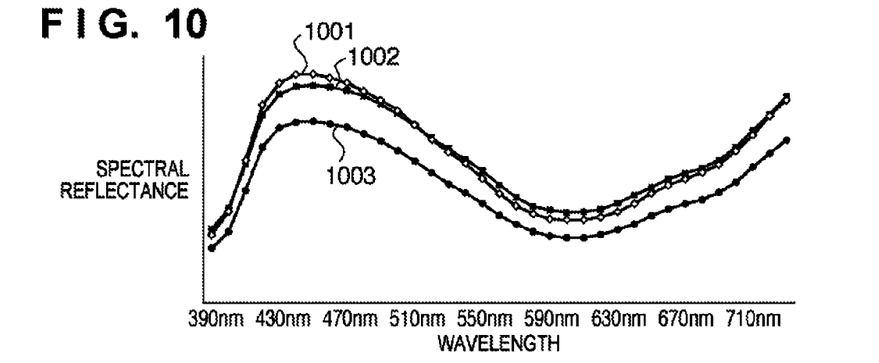
FIG. 10 is a graph showing an example of spectral reflectances of a blue color material, which are acquired by variable-angle measurements, according to the first embodiment.
Figure 11:
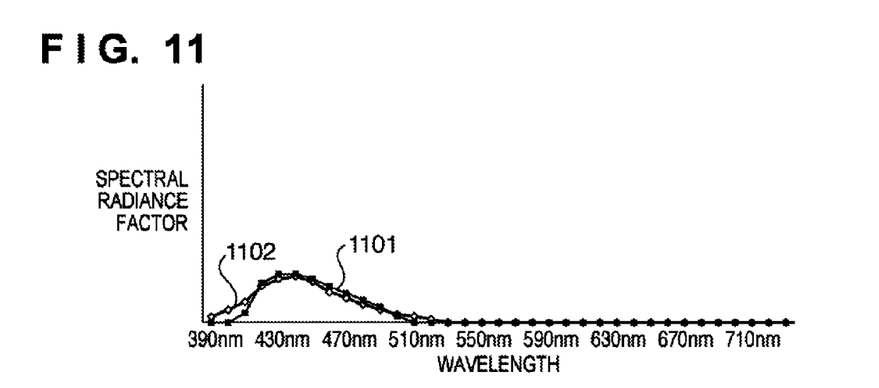
FIG. 11 is a graph showing an example of the spectral reflectances of fluorescence of the blue color material, which are estimated according to the first embodiment.

The graph of FIG. 8 described above shows the processing examples based on the variable-angle measurement data for the print medium containing the fluorescent substance. FIG. 10 shows processing examples based on variable-angle measurement data acquired by the variable-angle measurements as in FIG. 8 for a blue color material, which is applied on the print medium and contains a fluorescent substance. As shown in FIG. 10, the spectral reflectances of the fluorescent elements of the color material containing the fluorescent substance can be calculated as in the case of the print medium. That is, the fluorescent elements can be calculated based on two different types of variable-angle measurement data represented by spectral reflectance curves 1003 and 1002, and a spectral reflectance curve 1001 obtained by multiplying the spectral reflectance curve 1003 by the ratios n which allow the spectral reflectance curve 1003 to be equivalent to the spectral reflectance curve 1002 in the long-wavelength spectrum range. FIG. 11 shows a spectral radiance factor curve 1101 of the fluorescent elements acquired based on the spectral reflectance curves 1003 and 1002, and a spectral radiance factor curve 1102 of the fluorescent elements measured by the conventional method. As shown in FIG. 11, the spectral radiance factor curve 1101 of the fluorescent elements acquired by this embodiment nearly matches the spectral radiance factor curve 1102 of the fluorescent elements measured by the conventional method, and the wavelength characteristics of the fluorescent elements can also be acquired.

As described above, according to this embodiment, the two different variable-angle measurements are made for a print medium under the white light source which emits light in the spectrum range including the excitation spectrum range and fluorescent spectrum range of a fluorescent substance contained in the print medium, and the long-wavelength spectrum range outside the fluorescent spectrum range. Then, based on the measurement results, the spectral radiance factors of fluorescence produced by the sample are efficiently estimated.

An apparatus for acquiring the spectral radiance factors of fluorescence and its processing according to this embodiment will be described in detail below.

Spectral Reflectance Measuring Apparatus

Figure 3:
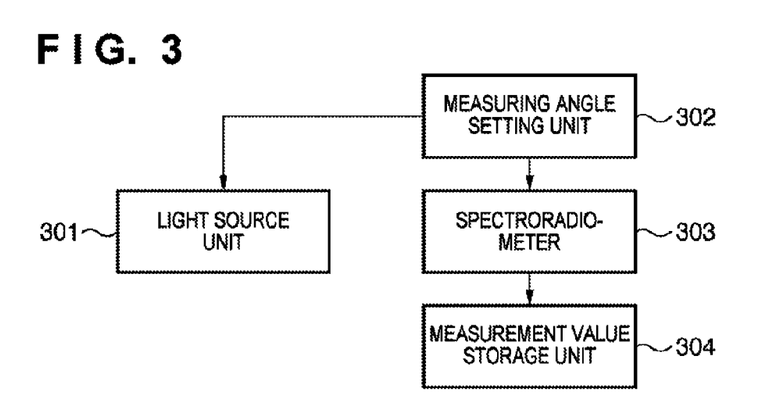
FIG. 3 is a block diagram showing the arrangement of a spectral reflectance measuring apparatus according to the first embodiment.

FIG. 3 is a block diagram showing the arrangement of a measuring apparatus for measuring spectral reflectances of a sample according to this embodiment. Note that this measuring apparatus corresponds to the input device 107 shown in FIG. 1. In the measuring apparatus of this embodiment, two different variable-angle measurements are made for a sample to acquire two different types of spectral reflectances. A measuring angle setting unit 302 sets two different angles (measuring angles) the positions of a measuring light source and a spectroradiometer 303 make with respect to the sample. As the two different measuring angles set by the unit 302, arbitrary angles may be set as long as a sufficient difference between spectral reflectance values of the sample measured at the two angles can be obtained. In this embodiment, the two different measuring angles are set to maximize the difference between the spectral reflectances to be measured. That is, as a first measuring angle, measuring angle 1 (angle of incidence: angle of reflection=45°:0°) at which only diffuse elements that do not contain any regular reflected elements of the light source are measured is set. Also, as a second measuring angle, measuring angle 2 (angle of incidence:angle of reflection=45°:45°) at which both the diffuse elements and regular reflected elements are measured is set. In the following description, each measuring angle is expressed by (angle of incidence:angle of reflection) using an angle of incidence and angle of reflection. For example, measuring angle 1 is (45:0), and measuring angle 2 is (45:45).

Note that since the two different measuring angles need only be set to obtain a sufficient difference between their measurement values, as described above, for example, measuring angle 2 may be set to be an angle which is closer to that at which regular reflected elements can be measured. Alternatively, an appropriate value may be set in advance as a difference between the two different measuring angles, and the measuring angles may be set based on the difference. For example, measuring angle 1 may be set as (45:15) and measuring angle 2 may be set as (45:45) to have 30° as the difference between the measuring angles.

After the measuring angle setting unit 302 sets measuring angles 1 and 2 as the measuring angles, the positions of a light source unit 301 as a measuring light source and a spectroradiometer 303 with respect to the sample are respectively adjusted to make measuring angles 1 and 2. Assume that the light source unit 301 in this embodiment is the white light source which emits light in the aforementioned broad spectrum range.

Figure 4:
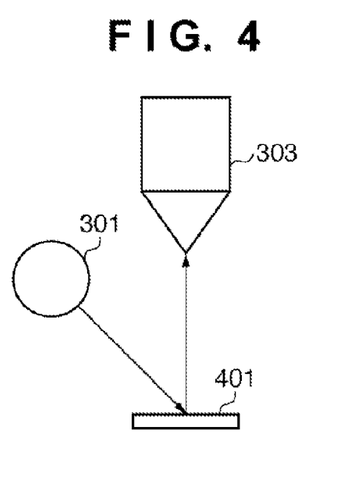
FIG. 4 is a view showing an example of a spectral radiance measuring angle according to the first embodiment.
Figure 5:
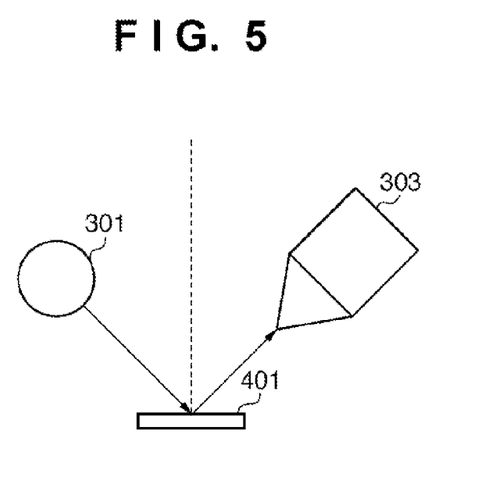
FIG. 5 is a view showing an example of a spectral radiance measuring angle according to the first embodiment.

FIG. 4 shows an example of the positional relationship between the light source unit 301 and spectroradiometer 303 with respect to a sample 401 upon making a measurement at measuring angle 1 (45:0). As shown in FIG. 4, the spectroradiometer 303 and light source unit 301 are arranged to respectively make angles of 0° and 45° with respect to a normal to a plane of the sample 401. FIG. 5 shows an example of the positional relationship between the light source unit 301 and spectroradiometer 303 with respect to the sample 401 upon making a measurement at measurement angle 2 (45:45). As shown in FIG. 5, the spectroradiometer 303 is arranged to make an angle of 45° with respect to the normal to the sample 401, and the light source unit 301 is arranged to make an angle of 45° symmetric to the spectroradiometer 303.

Figure 15:
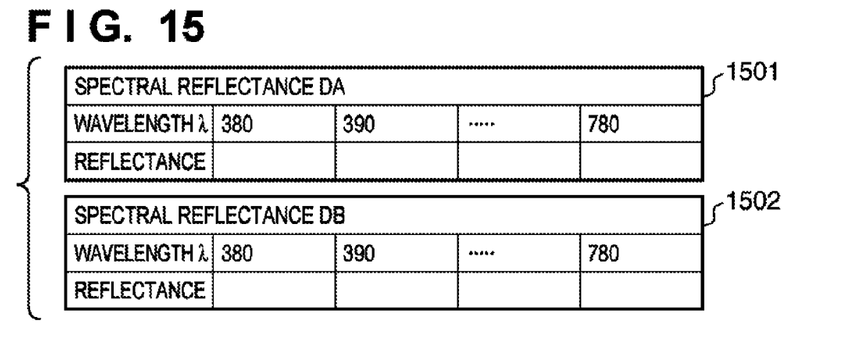
FIG. 15 is a view showing the memory configuration used to store the spectral reflectances acquired by variable-angle measurements in the first embodiment.

Variable-angle measurements of the sample 401 are made using the spectroradiometer 303 at measuring angles 1 and 2, which are set, as described above. Let $DA(\lambda)$ be a first spectral reflectance measured at measuring angle 1, and $DB(\lambda)$ be a second spectral reflectance measured at measuring angle 2. The spectral reflectances $DA(\lambda)$ and $DB(\lambda)$ of the sample 401 acquired by the variable-angle measurements of the spectroradiometer 303 are respectively stored in a measurement value storage unit 304 in a table format that holds reflectances for respective output wavelengths, as denoted by reference numerals 1501 and 1502 in FIG. 15.

Note that this embodiment has exemplified the case in which the variable-angle measurements of the sample are made using the spectroradiometer 303. Alternatively, a general goniophotometer may be used.

Fluorescent Estimating Processing

Fluorescent estimating processing for estimating spectral radiance factors of fluorescence produced from a sample based on two different types of spectral reflectances as variable-angle measurement data of the sample will be described in detail below.

Figure 6:
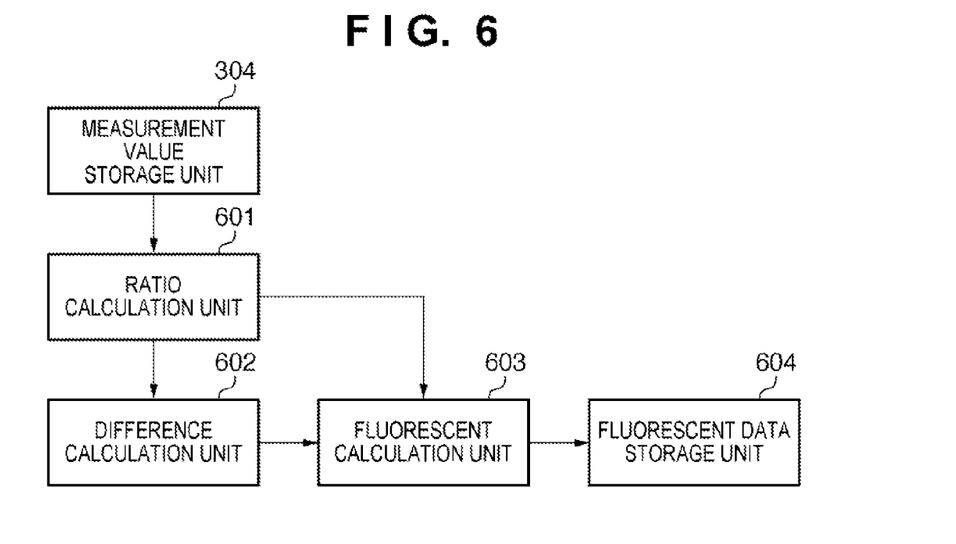
FIG. 6 is a block diagram showing the arrangement required to implement the fluorescent estimating processing according to the first embodiment.

FIG. 6 is a block diagram showing the arrangement required to implement the fluorescent estimating processing in the calculation processor 105 shown in FIG. 1. Note that the measurement value storage unit 304 shown in FIG. 6 stores the two different types of spectral reflectances $DA(\lambda)$ and $DB(\lambda)$ acquired by the variable-angle measurements of the measuring apparatus shown in FIG. 3. A ratio calculation unit 601 acquires the spectral reflectances $DA(\lambda)$ and $DB(\lambda)$ stored in the measurement value storage unit 304, and determines their magnitude relationship. In this embodiment, the ratio calculation unit 601 determines that the spectral reflectances $DB(\lambda)$ obtained by measuring the sample at measuring angle 2 at which regular reflected light is received are higher than the spectral reflectances $DA(\lambda)$ obtained by measuring the sample at measuring angle 1 at which only diffuse reflected light is received. Then, the ratio calculation unit 601 calculates ratios n to be multiplied by the spectral reflectances DA(λ) to minimize differences from the spectral reflectances DB(λ) in a long-wavelength spectrum range (580 to 780 nm in this embodiment) outside a spectrum range of fluorescence produced by the sample, using:

$$n = DB(\lambda)/DA(\lambda) \quad (4)$$

Note that the long-wavelength spectrum range for which the ratios n are calculated is arbitrarily set according to the spectrum range of fluorescence produced by the sample.

A difference calculation unit 602 calculates spectrum reflectances DF(λ) as differences between products obtained by multiplying the spectral reflectances DA(λ) by the ratios n calculated by the ratio calculation unit 601, and the spectral reflectances DB(λ) by:

$$DF(\lambda) = n \cdot DA(\lambda) - DB(\lambda) \quad (5)$$

A fluorescent calculation unit 603 calculates spectral radiance factors P(λ) of fluorescence of the sample based on the spectral reflectances DF(λ) as the differences acquired by the difference calculation unit 602, and the ratios n calculated by the ratio calculation unit 601 by:

$$P(\lambda) = (DF(\lambda)/(n-1)) \cdot \alpha \quad (6)$$

where α is an arbitrary coefficient used to adjust the range of the spectral radiance factors P(λ) of fluorescence.

Each spectral reflectance DF(λ) as the difference or spectral radiance factor P(λ) calculated using equation (5) or (6) may often assume a negative value for each wavelength. In such case, the obtained negative value is offset to zero.

Figure 16:
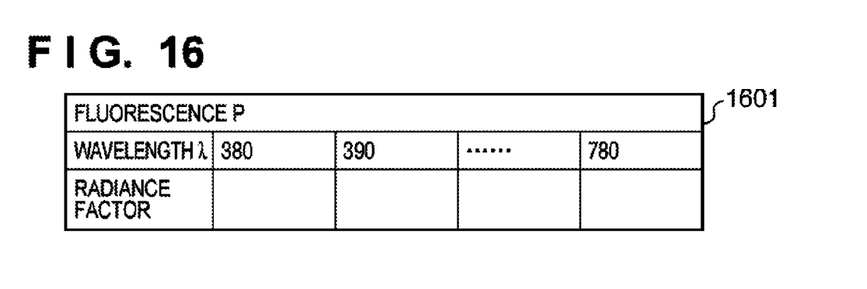
FIG. 16 is a view showing the memory configuration used to store the spectral radiance factors of fluorescence estimated in the first embodiment.

The spectral radiance factors P(λ) of fluorescence calculated by the fluorescent calculation unit 603, as described above, are stored in a fluorescent data storage unit 604 in a table format that holds radiance factors for respective output wavelengths, as denoted by reference numeral 1601 in FIG. 16.

Figure 2:
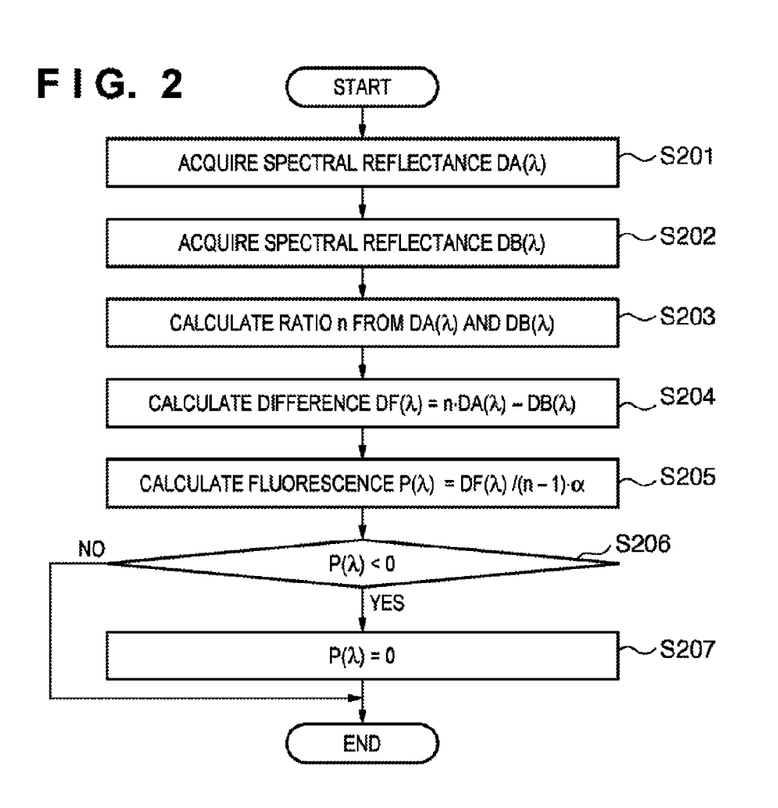
FIG. 2 is a flowchart showing fluorescent estimating processing according to the first embodiment.

The fluorescent estimating processing according to this embodiment will be described below with reference to the flowchart shown in FIG. 2. In steps S201 and S202, the ratio calculation unit 601 acquires spectral reflectances DA(λ) and DB(λ) of a sample measured at measuring angles 1 and 2. In step S203, the ratio calculation unit 601 acquires, using equation (4), ratios n to be multiplied by the spectral reflectances DA(λ) lower than the spectral reflectances DB(λ) so as to minimize differences from the spectral reflectances DB(λ) in the long-wavelength spectrum range in which no fluorescence is produced. Next, in step S204, the difference calculation unit 602 calculates spectral reflectances DF(λ) as differences between the values obtained by multiplying the spectral reflectances DA(λ) by the ratios n, and the spectral reflectances DB(λ) using equation (5). In step S205, the fluorescent calculation unit 603 calculates spectral radiance factors P(λ) of fluorescence based on the spectral reflectances DF(λ) as the differences acquired in step S204, and the ratios n acquired in step S203. That is, the spectral radiance factors of fluorescence are calculated by dividing the spectral reflectances DF(λ) as the differences by values obtained by subtracting 1 from the ratios n.

It is determined in step S206 for the spectral radiance factors P(λ) of fluorescence which are calculated in step S205 whether or not a radiance factor for each wavelength assumes a negative value. If the radiance factor for each wavelength assumes a negative value, it is offset to zero in step S207. The spectral radiance factors P(λ) of fluorescence acquired by the aforementioned processing are stored in the fluorescent data storage unit 604. Note that in the processing shown in FIG. 2, the sign of a radiance factor for each wavelength is determined for the acquired spectral radiance factors P(λ) of fluorescence. Alternatively, this sign determination may be made for the spectral reflectances DF(λ) as the differences acquired in step S204.

As described above, according to this embodiment, when two variable-angle measurements are made for a sample which is likely to contain a fluorescent substance under the white light source, the spectral radiance factors of fluorescence of the sample can be efficiently estimated from the measurement results. As a colorimeter used to make the variable-angle measurements, a general colorimeter, which does not especially require any special devices such as a plurality of light source devices, a spectroscope, and an amplifier, can be used.

Second Embodiment

The second embodiment according to the present invention will be described below. In general, color materials applied onto a print medium contain a fluorescent substance at different percentages depending on colors. Hence, whether or not to produce fluorescence depends on the colors. Hence, according to the feature of the second embodiment, whether or not to produce fluorescence is simply determined for a plurality of samples by the fluorescent estimating processing described in the aforementioned first embodiment upon measurements of fluorescence for the samples. That is, control is made to simply determine whether or not to produce fluorescence for each of the plurality of samples by the aforementioned fluorescent estimating processing, and to make detailed measurements of fluorescence for only the samples for which it is determined that fluorescence is produced.

Figure 12:
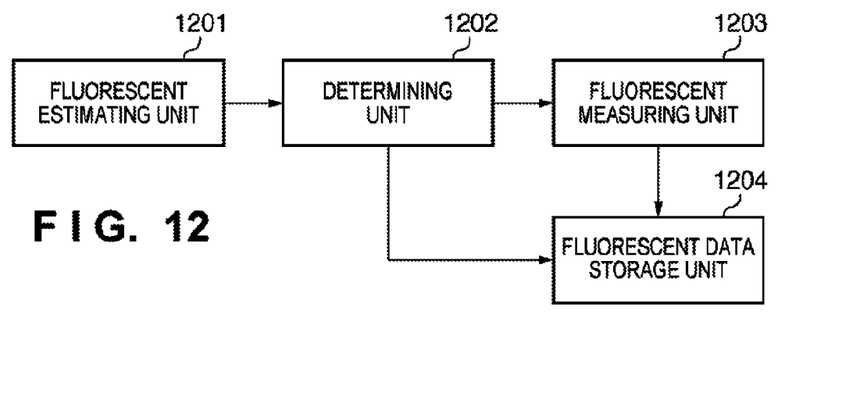
FIG. 12 is a block diagram showing the arrangement of a fluorescent measuring apparatus according to the second embodiment.

FIG. 12 is a block diagram showing the arrangement of a fluorescent measuring apparatus according to the second embodiment. A fluorescent estimating unit 1201 estimates spectral radiance factors of fluorescence for each of a plurality of samples by the fluorescent estimating processing described in the aforementioned first embodiment. A determining unit 1202 determines based on the spectral radiance factors of fluorescence estimated by the fluorescent estimating unit 1201 whether or not to produce fluorescence for each of the plurality of samples. For a sample for which it is determined that fluorescence is produced, a fluorescent measuring unit 1203 actually measures fluorescence, and actually measured spectral radiance factors are stored in a fluorescent data storage unit 1204. On the other hand, for a sample for which the determining unit 1202 determines that no fluorescence is produced, spectral radiance factors=0 of that fluorescence are stored in the fluorescent data storage unit 1204.

Figure 13:
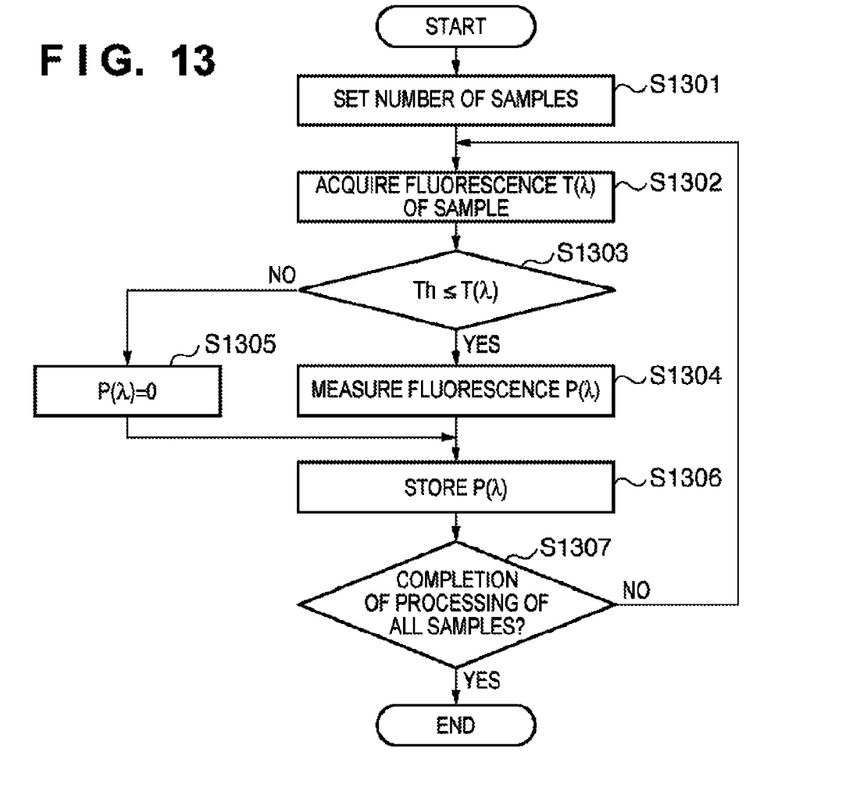
FIG. 13 is a flowchart showing fluorescent measuring processing according to the second embodiment.

Fluorescent measuring processing according to the second embodiment will be described below with reference to the flowchart shown in FIG. 13. In step S1301, the determining unit 1202 inputs the number of samples to be measured. In step S1302, the fluorescent estimating unit 1201 estimates spectral radiance factors T(λ) of fluorescence for a current sample of interest by the fluorescent estimating method described in the aforementioned first embodiment. In step S1303, the determining unit 1202 determines based on the spectral radiance factors T(λ) of fluorescence estimated in step S1302 whether or not to produce fluorescence in that sample. This determination is made, for example, as follows. That is, T(λ) is compared with a predetermined threshold Th in a fluorescent spectrum range. If T(λ) assumes a value equal to or larger than Th, it is determined that fluorescence is produced; if T(λ) assumes a value less than Th, it is determined that fluorescence is not produced.

If it is determined in step S1303 that the sample of interest produces fluorescence, the fluorescent measuring unit 1203 makes detailed fluorescent measurements for the sample of interest to acquire actually measured values of spectral radiance factors P(λ) of fluorescence in step S1304. In this case, as the detailed measurement method of the spectral radiance factors P(λ) of fluorescence, actual measurements may be made using a measuring device having a complicated arrangement regardless of the required number of processes, as described in the related art. On the other hand, if it is determined that the sample of interest does not produce any fluorescence, the determining unit 1202 sets spectral radiance factors P(λ) of fluorescence for the sample of interest to be zero in step S1305.

In step S1306, the spectral radiance factors P(λ) of fluorescence for the sample of interest, which are acquired in step S1304 or S1305, are stored in the fluorescent data storage unit 1204.

It is determined in step S1307 whether or not the processes in steps S1302 to S1306 are complete for samples as many as the number of samples set in step S1301. If samples to be processed still remain, the process returns to step S1302 to start the processing for the next sample.

As described above, according to the second embodiment, upon making fluorescent measurements for a plurality of samples, whether or not to produce fluorescence is simply determined for each sample by the fluorescent estimating method described in the first embodiment. Thus, detailed measurements can be made only for a sample which produces fluorescence, thus allowing efficient fluorescent measurements.

Other Embodiments

Note that the first embodiment has exemplified the case in which the spectral radiance factors of fluorescence of a sample are efficiently estimated. It is effective to inform the user of the estimation results using a predetermined UI. Especially, in the second embodiment, by displaying the estimation results on the UI, the user can easily recognize a sample for which actual measurements of fluorescence are to be made.

The present invention can also be implemented by executing the following processing. That is, in this processing, software (program) which implements the functions of the aforementioned embodiment is supplied to a system or apparatus via a network or various kinds of storage media, and a computer (or a CPU or MPU) of the system or apparatus reads out and executes the program.

This application claims the benefit of Japanese Patent Application No. 2010-183392, filed Aug. 18, 2010, which is hereby incorporated by reference herein in its entirety.

What is claimed is:

1. A fluorescent estimating apparatus comprising:
a first input unit configured to acquire first spectral reflectance characteristics which change depending on different measuring angles;
a second input unit configured to acquire second spectral reflectance characteristics which do not change depending on the different measuring angles; and
a calculation unit configured to calculate fluorescent elements based on the first spectral reflectance characteristics and the second spectral reflectance characteristics.

2. The apparatus according to claim 1,
wherein the different measuring angles are a first measuring angle and a second measuring angle,
wherein the first input unit further comprises:
an acquisition unit configured to acquire, for a sample which is likely to contain a fluorescent substance, first spectral reflectances measured at the first measuring angle as the first spectral reflectance characteristics, under a measuring light source which emits light in a spectrum range including an excitation spectrum range and a fluorescent spectrum range of the fluorescent substance, and a long-wavelength spectrum range outside the fluorescent spectrum range,
wherein the second input unit further comprises:
an acquisition unit configured to acquire, for the sample which is likely to contain a fluorescent substance, second spectral reflectances which are measured at the second measuring angle and are higher than the first spectral reflectances as the second spectral reflectance characteristics, under the measuring light source,
wherein the calculation unit further comprises:
a ratio calculation unit configured to calculate ratios of the second spectral reflectances to the first spectral reflectances in the long-wavelength spectrum range;
a difference calculation unit configured to calculate differences between products obtained by multiplying the first spectral reflectances by the ratios, and the second spectral reflectances; and
a fluorescent calculation unit configured to calculate spectral radiance factors of fluorescence of the sample based on the differences and the ratios.

3. The apparatus according to claim 2, wherein the first measuring angle is an angle at which diffuse reflected light, except for regular reflected light of the measuring light source from the sample, is measured, and
the second measuring angle is an angle at which the regular reflected light of the measuring light source from the sample is measured.

4. The apparatus according to claim 2, wherein the ratios assume values which minimize the differences between the products and the second spectral reflectances when the first spectral reflectances are multiplied by the ratios.

5. The apparatus according to claim 2, wherein the fluorescent calculation unit calculates the spectral radiance factors of fluorescence by dividing the differences by values obtained by subtracting 1 from the ratios.

6. The apparatus according to claim 2, wherein for each calculated spectral radiance factor that assumes a negative value, the fluorescent calculation unit sets that spectral radiance factor to be 0.

7. The apparatus according to claim 2, wherein for each calculated difference that assumes a negative value, the difference calculation unit sets that difference to be 0.

8. The apparatus according to claim 2, further comprising a determining unit configured to determine whether or not to produce fluorescence in the sample based on the spectral radiance factors of fluorescence of the sample calculated by the fluorescent calculation unit.

9. A control method of a fluorescent estimating apparatus, comprising:
a first input step of acquiring first spectral reflectance characteristics which change depending on different measuring angles;
a second input step of acquiring second spectral reflectance characteristics which do not change depending on the different measuring angles; and
a calculation step of calculating fluorescent elements based on the first spectral reflectance characteristics and the second spectral reflectance characteristics.

10. The control method according to claim 9,
wherein the different measuring angles are a first measuring angle and a second measuring angle, wherein the first input step further comprises:
    acquiring, for a sample which is likely to contain a fluorescent substance, first spectral reflectances measured at the first measuring angle as the first spectral reflectance characteristics, under a measuring light source which emits light in a spectrum range including an excitation spectrum range and a fluorescent spectrum range of the fluorescent substance, and a long-wavelength spectrum range outside the fluorescent spectrum range,
wherein the second input step further comprises:
    acquiring, for the sample which is likely to contain a fluorescent substance, second spectral reflectances which are measured at the second measuring angle and are higher than the first spectral reflectances as the second spectral reflectance characteristics, under the measuring light source,
wherein the calculation step further comprises:
    calculating ratios of the second spectral reflectances to the first spectral reflectances in the long-wavelength spectrum range;
    calculating differences between products obtained by multiplying the first spectral reflectances by the ratios, and the second spectral reflectances; and
    calculating spectral radiance factors of fluorescence of the sample based on the differences and the ratios.

11. The control method according to claim 10, wherein the first measuring angle is an angle at which diffuse reflected light except for regular reflected light of the measuring light source from the sample is measured, and
    the second measuring angle is an angle at which the regular reflected light of the measuring light source from the sample is measured.

12. The control method according to claim 10, wherein the ratios assume values which minimize the differences between the products and the second spectral reflectances when the first spectral reflectances are multiplied by the ratios.

13. The control method according to claim 10, wherein the calculation step further comprises calculating the spectral radiance factors of fluorescence by dividing the differences by values obtained by subtracting 1 from the ratios.

14. The control method according to claim 10, wherein for each calculated spectral radiance factor that assumes a negative value, that spectral radiance factor is set to be 0.

15. The apparatus according to claim 10, wherein for each calculated difference that assumes a negative value, that difference is set to be 0.

16. The apparatus according to claim 10, further comprising a determining step of determining whether or not to produce fluorescence in the sample based on the spectral radiance factors of fluorescence of the sample calculated in the calculation step.

* * * * *